(12) United States Patent
Barrows

(10) Patent No.: US 9,072,818 B2
(45) Date of Patent: Jul. 7, 2015

(54) BIOMATERIALS MADE FROM HUMAN HAIR

(75) Inventor: Thomas H. Barrows, Austell, GA (US)

(73) Assignee: Cell Constructs I, LLC, Atlanta, GA (US)

( * ) Notice: Subject to any disclaimer, the term of this patent is extended or adjusted under 35 U.S.C. 154(b) by 0 days.

(21) Appl. No.: 13/520,114

(22) PCT Filed: Jan. 3, 2011

(86) PCT No.: PCT/US2011/020043
§ 371 (c)(1),
(2), (4) Date: Jun. 29, 2012

(87) PCT Pub. No.: WO2011/084925
PCT Pub. Date: Jul. 14, 2011

(65) Prior Publication Data
US 2012/0276188 A1 Nov. 1, 2012

Related U.S. Application Data

(60) Provisional application No. 61/292,265, filed on Jan. 5, 2010.

(51) Int. Cl.
| | |
|---|---|
| A61K 35/36 | (2006.01) |
| A61K 9/70 | (2006.01) |
| A61P 17/00 | (2006.01) |
| A61K 35/12 | (2006.01) |
| A61L 27/38 | (2006.01) |
| A61K 35/28 | (2015.01) |
| A61L 27/36 | (2006.01) |
| A61L 27/52 | (2006.01) |
| C12N 5/00 | (2006.01) |

(52) U.S. Cl.
CPC ............. *A61L 27/3834* (2013.01); *A61K 35/28* (2013.01); *A61K 35/36* (2013.01); *A61L 27/3604* (2013.01); *A61L 27/52* (2013.01); *A61L 2430/18* (2013.01); *C12N 5/0068* (2013.01); *C12N 2533/50* (2013.01)

(58) Field of Classification Search
CPC ......... A61K 35/28; A61K 35/36; A61L 27/52
See application file for complete search history.

(56) References Cited

U.S. PATENT DOCUMENTS

| | | | |
|---|---|---|---|
| 5,830,708 A | 11/1998 | Naughton | |
| 5,932,552 A | 8/1999 | Blanchard et al. | |
| 5,972,332 A | 10/1999 | Rees et al. | |
| 5,980,888 A | 11/1999 | Dimoudis et al. | |
| 6,086,863 A | 7/2000 | Ritter et al. | |
| 6,110,487 A * | 8/2000 | Timmons et al. | 424/443 |
| 6,159,496 A | 12/2000 | Blanchard et al. | |
| 6,264,943 B1 | 7/2001 | Cherksey | |
| 6,299,898 B2 | 10/2001 | Rees et al. | |
| 6,316,598 B1 | 11/2001 | Van Dyke et al. | |
| 6,419,920 B1 | 7/2002 | Mineau-Hanschke | |
| 6,440,452 B2 | 8/2002 | Rees et al. | |
| 6,461,628 B1 * | 10/2002 | Blanchard et al. | 424/402 |
| 7,001,987 B2 | 2/2006 | Van Dyke | |
| 7,419,661 B2 | 9/2008 | Jahoda et al. | |
| 7,470,537 B2 | 12/2008 | Hedrick et al. | |
| 7,651,684 B2 | 1/2010 | Hedrick et al. | |
| 7,736,669 B2 | 6/2010 | Zhang et al. | |
| 7,767,452 B2 | 8/2010 | Kleinsek | |
| 7,795,027 B2 | 9/2010 | Hiles | |
| 2001/0032019 A1 | 10/2001 | Van Dyke et al. | |
| 2002/0015725 A1 | 2/2002 | Rees et al. | |
| 2003/0065389 A1 | 4/2003 | Petersen | |
| 2003/0187115 A1 | 10/2003 | Cinelli et al. | |
| 2005/0074482 A1 | 4/2005 | Goldman et al. | |
| 2007/0111937 A1 * | 5/2007 | Pickar et al. | 514/12 |
| 2007/0185463 A1 | 8/2007 | Mulligan | |
| 2007/0275077 A1 | 11/2007 | Arias | |
| 2008/0089930 A1 | 4/2008 | Siller-Jackson et al. | |
| 2009/0047260 A1 | 2/2009 | Van Dyke | |
| 2009/0110731 A1 | 4/2009 | Fritz et al. | |
| 2009/0246282 A1 | 10/2009 | Kluijtmans et al. | |

FOREIGN PATENT DOCUMENTS

| | | |
|---|---|---|
| EP | 0448770 | 7/1990 |
| EP | 1051982 | 11/2000 |

OTHER PUBLICATIONS

Borrelli et al., "In Vitro Characterization and Ex Vivo Surgical Evaluation of Human Hair Keratin Films in Ocular Surface Reconstruction After Sterilization Processing", Journal of materials Science: Materials in Medicine, vol. 24, pp. 221-230 (2013).
Aboushwareb et al., "A Keratin Biomaterial Gel Hemostat Derived from Human Hair: Evaluation in a Rabbit Model of Lethal Liver Injury", Journal of Biomedical Materials Research Part B: Applied Biomaterials, pp. 45-54 (2008).
Akasha et al., "Entrapment of Embryonic Stem Cells-Derived Cardiomyocytes in Macroporous Biodegradable Microspheres: Preparation and Characterization", Cellular Physiology and Biochemistry, vol. 22, pp. 665-672 (2008).
Adhirajan et al., "Functionally Modified Gelatin Microspheres Impregnated Collagen Scaffold as Novel Wound Dressing to Attenuate the Proteases and Bacterial Growth", European Journal of Pharmaceutical Sciences, vol. 36, pp. 235-245 (2009).
Barry et al., "Mesenchymal Stem Cells: Clinical Applications and Biological Characterization", The International Journal of Biochemistry & Cell Biology, vol. 36, pp. 568-584 (2004).
Choi et al., "Human Extracellular Matrix (ECM) Powders for Injectable Cell Delivery and Adipose Tissue Engineering", Journal of Controlled Release, vol. 139, pp. 2-7 (2009).
Chung et al., "Injectable Cellular Aggregates Prepared from Biodegradable Porous Microspheres for Adipose Tissue Engineering", Tissue Engineering: Part A, vol. 15(6), pp. 1391-1400 (2009). (Abstract only).

(Continued)

*Primary Examiner* — Kyle Purdy
(74) *Attorney, Agent, or Firm* — Meunier Carlin & Curfman LLC

(57) ABSTRACT

A hydrogel that comprises denatured human hair biomolecules intermolecularly crosslinked with disulfide bonds to form a hydrogel. The hydrogel may be prepared by reduction and denaturation of hair to provide keratins and other hair biomolecules that are crosslinked by the disulfide bonds to provide a firm, flexible, and useful biomaterial.

29 Claims, 6 Drawing Sheets

(56) References Cited

OTHER PUBLICATIONS

De Guzman et al., "Mechanical and Biological Properties of Keratose Biomaterials", Biomaterials, vol. 32, pp. 8205-8217 (2011).
Eibes et al., "Maximizing the ex vivo Expansion of Human Mesenchymal Stem Cells Using a Microcarrier-Based Stirred Culture System", Journal of Biotechnology, vol. 146, pp. 194-197 (2010).
Fujii et al., "Convenient Procedures for Human Hair Protein Films and Properties of Alkaline Phosphatase Incorporated in the Film", Biological and Pharmaceutical Bulletin, vol. 27(1), pp. 89-93 (2004).
Fujii et al. "Preparation of Translucent and Flexible Human Hair Protein Films and Their Properties" Biological Pharmaceutical Bulletin, vol. 27(9), pp. 1433-1436 (2004).
Hermanson, "Bioconjugate Techniques", Elsevier Science, 15 pages (1996). (Covers and Index only).
Hill et al., "Some Properties of Keratin Biomaterials: Kerateines", Biomaterials, vol. 31, pp. 585-593 (2010).
Kim et al., "Gas Foamed Open Porous Biodegradable Polymeric Microspheres", Biomaterials, vol. 27, pp. 152-159 (2006).
Nakamura et al., "A Rapid Extraction Procedure of Human Hair Proteins and Idenification of Phosphorylated Species" Biological and Pharmaceutical Bulletin, vol. 25(5), pp. 569-572 (2002).
Natesan et al. "Adipose-Derived Stem Cell Delivery into Collagen Gels Using Chitosan Microspheres", Tissue Engineering: Part A, vol. 16(4), pp. 1369-1385 (2009).
Nie et al., "Local Delivery of Adipose-Derived Stem Cells Via Acellular Dermal Matrix as a Scaffold: A New Promising Strategy to Accelerate Wound Healing", Medical Hypotheses, vol. 72, pp. 679-682 (2009).
Reichl, "Keratin Coated Surfaces as Growth Substrate—A Novel Approach to Stimulate Cell Proliferation in Culture", 5th World Meeting on Pharmaceutics, Biopharmaccutics and Pharmaceutical Technology,1 Page (2006).
Reichl, "Films Based on Human Hair Keratin as Substrates for Cell Culture and Tissue Engineering", Biomaterials, vol. 30, pp. 6854-6866 (2009).
Richter et al., "Mechanisms of Hepatocyte Attachment to Keratin Biomaterials", Biomaterials, vol. 32, pp. 7555-7561 (2011).
Rouse et al., "A Review of Keratin-Based Biomaterials for Biomedical Applications", Materials, vol. 3, pp. 999-1014 (2010).
Salinas et al., "The Influence of the RGD Peptide Motif and its Contextual Presentation in PEG Gels on Human Mesenchymal Stem Cell Viability", Journal of Tissue Engineering and Regenerative Medicine, vol. 2, pp. 296-304 (2008).
Saul et al., "Keratin Hydrogels Support the Sustained Release of Bioactive Ciprofloxacin", Journal of Biomedical Materials Research, vol. 98A, Issue 4, pp. 544-553 (2011).
Verma et al., "Preparation of Scaffolds from Human Hair Proteins for Tissue-Engineering Applications", Biomedical Materials, vol. 3, 8 Pages (2008).
International Search Report and Written Opinion from Corresponding PCT Application No. PCT/US2011/020043 Dated Sep. 9, 2011, 14 pages.

* cited by examiner

BIOMATERIALS MADE FROM HUMAN HAIR

CROSS REFERENCE TO RELATED APPLICATIONS

This application claims priority to PCT Application No. PCT/US2011/020043 filed Jan. 3, 2011 which claims priority to U.S. Provisional Ser. No. 61/292,265 filed Jan. 5, 2010, each of which are hereby incorporated herein by reference.

TECHNICAL FIELD

The Technical Field includes biomedical materials that use keratin or hair-derived proteins, as well as methods of using these materials in the life science arts, for instance, for wound healing.

BACKGROUND

The field of tissue engineering has the goal of regenerating or replacing tissue lost to disease or injury by implantation of cultured cells. Most cells that are useful for this purpose are attachment dependant, meaning that they will not survive unless bound to some type of solid surface. Within the human body attachment-dependant cells are attached to a natural scaffold material known as the extracellular matrix (ECM). Thus a tissue-engineered implant typically comprises cells that have been seeded on an artificial scaffold.

Some recent advances in the field of tissue engineering have focused on synthetic polymeric materials that are compatible with cell attachment. Since many synthetic polymerizable materials, e.g., poly(hydroxyethyl methacrylate) (pHEMA) are cell repellant, such materials may typically incorporate biopolymers such as collagen, laminin, fibronectin, hyaluronic acid, or other proteins and/or polysaccharides calculated to enhance cell attachment. Alternatively, specific cell binding moieties such as arginine-glycine-aspartic acid (RGD) peptide motifs may be grafted onto the hydrogel to confer cell attachment potential.

Keratins found in human and other animal hair have attracted interest as a potential biomaterial. Keratins, however, are tightly bound to each other so that recovering keratin biomolecules is difficult.

SUMMARY

An embodiment of the invention is a material comprising denatured hair biomolecules intermolecularly crosslinked with disulfide bonds to form a flexible and/or bendable hydrogel network, with the disulfide bonds being present in a concentration effective to provide the network with a modulus of more than about 100 Pa.

An embodiment of the invention is a material system comprising denatured human hair biomolecules intermolecularly crosslinked with disulfide bonds to form a hydrogel with a modulus of more than about 100 Pa, with the hydrogel being substantially free of other chemical crosslinks between the human hair biomolecules.

An embodiment of the invention is a process of making a hydrogel comprising placing human hair in a reducing solution that breaks intermolecular bonds between keratin proteins in the hair, exposing the solution to an oxidizing agent, and removing the reducing solution, leaving a hydrogel comprising a network of keratins crosslinked to each other with disulfide bonds.

An embodiment of the invention is a biomedical system for treating a wound comprising a hydrogel that comprises denatured human hair biomolecules intermolecularly crosslinked with disulfide bonds to form the hydrogel with a modulus of more than about 100 Pa.

An embodiment of the invention is a method comprising culturing cells on a hydrogel having an elastic modulus of at least about 100 Pa, and applying the hydrogel to a tissue.

An embodiment of the invention is a construct for hair growth comprising a hair coated with a hydrogel and comprising dermal stem cells and epidermal stem cells in contact with the hydrogel, with the hair and cells being from the same donor.

An embodiment of the invention is a method of processing hair constructs comprising obtaining stem cells from a donor, multiplying the stem cells, and seeding them on a plurality of hydrogel-coated hairs from the same donor.

An embodiment of the invention is directed to hydrogels made substantially only from hair-derived materials. The hydrogel may be essentially free of non-hair ingredients. The cysteine residues of the hydrogel may be substantially disposed as either participants in a disulfide bond or free sulfhydryls, with these residues not being derivatized. The hydrogel may be substantially free of sulfonic acid and sulfinic acid. The hydrogel may be substantially free of cysteic acid. The network of the hydrogel may provide at least about 90% of the network, as measurable by dry w/w. The hydrogels may have a therapeutic agent, either free or covalently attached.

DETAILED DESCRIPTION

Figure 1:
FIG. 1 is a photograph of a keratinous hydrogel sheet with discs cut therefrom and removed using a 6-mm diameter dermal biopsy punch.

An embodiment of the invention is a hydrogel made of denatured hair biomolecules, namely, keratins and the other biomolecules found in human hair. This hydrogel may be made in a pure form with non-derivatized keratin that is free of non-autologous materials but is nonetheless strong and flexible.

In contrast, it is believed that conventional approaches based on use of a pure keratin or pure hair-based materials do not provide a hydrogel, and are further limited to non-hydrogel materials that are weak and brittle. Alternative conventional approaches require adding chemical groups to keratin or blending exogenous synthetic materials with the keratins to make a material that is more than merely loose and fragile.

Introduction and Disclosure

In general, there are two approaches to extracting proteins from hair, which is exceptionally resistant to solvents due to its disulfide (cystine) crosslinked chemical structure. One approach is to break the intermolecular disulfide bonds by oxidation (cystine to cysteic acid) and the other is to break the disulfide bonds by reduction (cystine to cysteine). The oxidation process begins with exposure of the hair to an oxidizing agent that converts each disulfide into two sulfate groups, i.e. cysteic acid residues. Once oxidized, typically with peracetic acid, the hair must then be rinsed free of excess oxidizing agent and subsequently solubilized and extracted under alkaline conditions, often with added reducing agent to reductively cleave remaining intact disulfide crosslinks. An example of this procedure is disclosed in U.S. Pat. No. 6,159,496 to Blanchard, et al., entitled "Keratin-Based Hydrogel for Biomedical Applications and Method of Production", which is hereby incorporated herein by reference for all purposes; in case of conflict, the specification is controlling.

Blanchard, et al. further discloses obtaining hydrogel by extracting oxidized hair with thioglycolate. Hydrogels related to the Blanchard hydrogel are disclosed for example in *Journal of Biomedical Materials Research Part B: Applied Biomaterials*, vol. 90B, pages 45-54, 2009 to T. Aboushwareb, et al entitled "A Keratin Biomaterial Gel Hemostat Derived from Human Hair: Evaluation in a Rabbit Model of Lethal Liver Injury", incorporated herein by reference, obtained with a similar method. The thioglycolate extraction method imparts chemically produced hydrophilic anionic groups to the keratin proteins in the form of cysteine-thioglycolate disulfide derivatization. The term derivitized, as used herein, refers to making a permanent substitution or addition to a chemical group. Subsequent hydrogel formation based upon natural oxidative re-formation of disulfide linkages in keratin thus solubilized typically affords only a weak gel due to the loss of a substantial percentage of available sulfhydryl groups by said thioglycolate derivatization.

The reducing agent only approach is less effective unless performed using strong protein denaturing conditions such as a high concentration of urea, which breaks intra- and intermolecular hydrogen bonds. Nevertheless, thioglycolate alone (e.g. aqueous ammonium thioglycolate solution) can be used to obtain the more easily extractable fractions of hair proteins. This is the same reagent used in highly diluted form in hair salons to soften hair to create a "perm", which is then "set" into a desired style by neutralization of the reducing agent with dilute hydrogen peroxide.

An effective reagent for reductive cleavage of keratin protein disulfide linkages is mercaptoethanol, a reagent commonly employed in analytic biochemistry to solubilize disulfide crosslinked proteins. A well established protocol for obtaining a high yield of all but the most intractable constituents of hair is known as the "Shindai Method" described in Nakamura, et al. entitled "A Rapid Extraction Procedure of Human Hair Proteins and Identification of Phosphorylated Species", *Biol Pharm Bull*, 25(5), 569-572, 2002, incorporated herein by reference. This method involves extraction of hair in a pH 8.5 buffered solution containing 5M urea, 2.5M thiourea, and 5% mercaptoethanol at 50° C. for 3 days. The Shindai method has been employed in the preparation of porous non-hydrogel films comprised of keratin in the form of particles, filaments, and porous structures described in Fujii, et al. entitled "Convenient Procedures for Human hair Protein Films and Properties of Alkaline Phosphatase Incorporated in the Film", *Biol Pharm Bull*, 27(1), 89-93, 2994, incorporated herein by reference.

The Shindai method treatment of a hair sample results in a solute of denatured hair in a solvent of the Shindai solution. This solute, however, can only be kept in solution in an extreme chemical environment; there exists a problem of not being able to keep the extracted proteins in solution upon removal of the mercaptoethanol. Dialysis to remove the urea, thiourea, and mercaptoethanol for example results in precipitation of a substantial portion of the dissolved proteins. Moreover, any attempt at dilution of the Shindai protein extract with greater than an equal volume of the same concentration of mercaptoethanol in the absence of urea also causes precipitation. As a result, the kinds of materials that can be made with keratin recovered by the Shindai method are significantly limited. Since these materials tended to precipitate, for instance, they could readily be made into films of aggregated proteins. But it was not known how to parlay proteins processed by a Shindai method into a hydrogel.

Hydrogels

Serendipitously, however, it was discovered that hair in a Shindai solution could be treated so that it could form a hydrogel. The discovery was that exposure to a small amount of air and concentration of the solution would create a strong, flexible, and elastic hydrogel. Further experiments indicate that various oxidizing agents may be used besides, or in addition to, the oxygen in air. The hydrogel may be made to be firm and elastic to have good properties for handling, shaping, processing, and use as a biomaterial. Further tests have shown its usefulness for cell culture and other applications. The properties may all be accomplished with a pure hydrogel of denatured hair biomolecules that is free of exogenous and/or derivitizing materials and is well suited for autologous treatments and cell cultures.

Certain embodiments of the invention are directed to a hydrogel comprising denatured hair biomolecules intermolecularly crosslinked with disulfide bonds to form a hydrogel. An advantage of using these proteins and associated biomolecules is that they are not derivitized. The proteins are in a soluble form without the use of thioglycolate or other reagents that impart chemical modification to the proteins or otherwise interfere with the accessibility of the natural sulfhydryl functional groups.

A hydrogel is a network of crosslinked hydrophilic polymer chains that are water-insoluble. Hydrogels may contain a large amount of water, e.g. greater than about 40%. In contrast, an aggregation of proteins or a film of agglomerated biomolecules is not a hydrogel. The term crosslinked means that the polymer chains have an average of more than about two linkages to another chain. The crosslinks may be physical or chemical. The term physical refers to hydrophobic-hydrophilic bonds, binds through polarity or Van der Waals forces, aggregation or coacervation effects, and ionic binding or ionic complex formation. The term chemical refers to covalent and disulfide bonds. Covalent bonds are chemically and functionally distinct from physical bonds, and these differences have implications for hydrogel structure and function, including solubility, durability, elastic modulus, degradability, and swelling.

The character of a hydrogel network contributes to a hydrogel's physical properties such as strength, elastic modulus, and flexibility. The network is the polymers that are crosslinked together to form the hydrogel. The distance between crosslinks relates to flexibility and the number and nature of the crosslinks relates to strength. The Young's modulus (also referred to as modulus of elasticity, or modulus) is a ratio of stress (force per unit area) to strain (length change per length) and has units of force per area, typically Newtons per square meter, abbreviated as Pa (for Pascal). The network may have a modulus, with further additions to the hydrogel altering the modulus or other properties of the overall material to some degree. The modulus of a network may be determined by measuring it in the absence of any such further additions.

The hydrogels may be made with a modulus of more than about 100 Pa. By way of comparison, other moduli are: less than 1 kPa for a typical swollen agarose gel, about 0.7 kPa for most consumer formulations of JELL-O, about 0.1 to 1 kPa for brain tissue, about 8 to 17 for muscle tissue, about 25 kPa for a typical collagen gel, and about $15(10)^6$ kPA for bone. The hair biomolecule hydrogels described herein may be provided with a variety of elastic behavior, e.g., from about 100 Pa to about 100 kPa; artisans will immediately appreciate that all the ranges and values within the explicitly stated range are contemplated, e.g., more than about 100 Pa or from about 100 Pa to about 100 kPa, or more than about 500 Pa. The hydrogels may be made to be flexible, a term that, as used herein, means having a flexibility for manual manipulation without tearing or breaking. The test for flexibility is to prepare a sample 1 cm wide by 5 cm long by 1 mm high, and suspend the sample by an area on one end that is 0.5 cm by 0.5 cm. If the sample breaks or tears, it is not flexible. The hydrogel may be made to be bendable; the 5 cm long rectangular sample may be bent back on itself so that the short ends of the rectangle meet without breaking or tearing the hydrogel.

The denatured hair biomolecules may be prepared with the Shindai method, which involves placing hair in a pH 8.5 buffered solution of about 5 M urea, about 2.5 M thiourea, and about 5% mercaptoethanol at about 50° C. for at least about 2 days to reduce the hair. The term denatured hair biomolecule refers to a biomolecule derived from hair by a process that breaks apart the crosslinking bonds in natural hair. These hair biomolecules include keratins known to be present in a human hair sample as well as other proteins and materials. The hair molecules may optionally be filtered to remove relatively low molecular weight components, e.g., with a cut-off of from 5,000 to 20,000 Daltons; artisans will immediately appreciate that all the ranges and values within the explicitly stated ranges are contemplated, e.g., an about 10,000 molecular-weight cut-off. In general, a hair sample (human or other mammalian) is placed in a treatment solution with a reducing agent and a denaturant. The hair is left in the solution until a visibly substantial portion is dissolved, e.g., 10 to 100 hours (artisans will immediately appreciate that all the ranges and values within the explicitly stated ranges are contemplated) and the remaining portion may be discarded. The solution may be heated, e.g., at between 30° C. and 100° C.; artisans will immediately appreciate that all the ranges and values within the explicitly stated ranges are contemplated, e.g. at about 50° C. The treatment solution is a chemical mixture that is effective to reduce and denature hair under reducing conditions. It may have one or more reducing agents, for instance, mercaptoethanol, thiourea, and compounds having a thiol group. The denaturant is a strong solution of one or more denaturants. Examples are urea and thiourea. Denaturants and reducing agents may be present at a concentration of at least about 2% v/v for a liquid and at least about 0.5 M for a solid.

Working Example 1 (see FIG. 1) describes a hydrogel prepared by these techniques. The hair sample was prepared in a treatment solution that denatured and reduced the hair sample. The treatment solution was concentrated and exposed to an oxidizing agent. The resultant hydrogels were washed thoroughly to remove all of the treatment solution and other chemicals. The concentration step may be performed so as to bring the solution just to the point where urea begins to crystallize. A high concentration of denatured hair protein solution is desired to achieve a high modulus hydrogel. One technique is to perform the process repeatedly and establish times and/or volumes of liquid where this point is reached. Another approach is to visually monitor the concentration process and look for signs the crystallization is about to occur. Optionally, an additional step to further facilitate concentration prior to the steps of oxidation and washing is to induce urea crystal formation in the un-concentrated treatment solution by cooling to 4° C. and storing at this temperature until urea crystallization occurs. It was discovered that cooling the treatment solution and removing of a portion of the original urea content via cold-induce crystallization does not cause the solubilized hair to precipitate. The cold solution is then filtered or decanted from the crystals and the supernatant subjected to ultra-filtration to give a concentrated solution that can be further concentrated by evaporation to a greater degree than possible without this additional step, i.e. more liquid can be evaporated prior to the appearance of crystals of residual urea. Another approach is demonstrated in Example 3, which provides for concentration by solvent/solvent removal. The treatment solution was exposed to another solvent that, without being bound to a particular theory, apparently removed some portions of the treatment solution, probably mercaptoethanol. The oxidation process may be performed in a humid (e.g., 100% relative humidity) environment to preferentially evaporate non-water solvents and allow ambient oxygen to permeate the solution for a protracted period of time (e.g. overnight) without causing excessive drying that might otherwise induce unwanted urea crystallization.

In Example 1, samples were exposed to air by being poured onto a surface and allowed to partially dry. Others were further exposed to an oxidizing agent (hydrogen peroxide) during a subsequent rehydration step. In Example 3, the concentrated solution ($HPE_c$) in the form of droplets suspended in oil was exposed to an oxidizing agent mixed with the oil (e.g. benzoyl peroxide) and likely also experienced oxidation by transfer of mercaptoethanol out of the aqueous phase into the oil phase. The oxygen in air is an oxidizing agent and also is present dissolved in water and to a lesser extend in vegetable oil. In addition to hydrogen peroxide, other water soluble oxidizing agents may be, e.g., potassium persulfate, potassium permanganate, perchloric acid, chromate and dichromate salts, and ozone. Useful oxidizing agents that have some solubility in oil, especially vegetable oils, include benzoyl peroxide, t-butyl hydroperoxide, and cumene hydroperoxide. The concentration of oxidizing agent may be controlled to provide a limited amount to the hair in the treatment solution, for example by limiting the agent to exposure to gaseous oxygen that must transfer from the gas phase into the liquid solvent. Another option is to use a liquid or solid oxidizing agent at a concentration of about 3% in the case of hydrogen peroxide in water and about 0.5% in the case of benzoyl peroxide in vegetable oil. Embodiments include processes wherein the oxidizing agent, prior to being combined with the reducing solution, is a liquid or a solid at 20° C. and is placed in the reducing solution at a concentration of about 1% to about 5% by volume if liquid and 0.25% to about 2% by weight per volume if solid.

Example 2 demonstrates how other hair derived materials could not be made into a hydrogel. Hair products generated by oxidation of hair were obtained and treated the same as the hair products used in Example 1. Nonetheless, only a weak jelly-like material was obtained. Without being bound to a particular theory, the initial oxidation process used to render the hair soluble is believed to have substantially derivatized the keratins in the hair, to the point that there were not enough free sulfhydryls left to form an adequate concentration of disulfide bonds required for hydrogel formation.

The hydrogels were also formed as particles. Example 3 (see FIG. 2A) details a process for making microspheres. Hair in an aqueous treatment solution was concentrated and dispersed as droplets into a hydrophobic medium (or continuous phase, with the droplets being the dispersed phase). An oxidizing agent was present in the hydrophobic phase. The denatured hair biomolecules in the dispersed solution turned into hydrogels. Other processes may be used for forming droplets, for instance, emulsions or spraying. For example, the treatment solution with the hair may be sprayed through air or other gas phase. These processes may be controlled to make materials of a desired size, for instance by controlling nozzle sizes and rates. Or stirring and mixing may be controlled to make droplet dispersions of a desired size. Examples of particle size are: a particle with a length passing through a central point of 1 µm to 1 mm; artisans will immediately appreciate that all the ranges and values within the explicitly stated ranges are contemplated, e.g., 10 µm to 100 µm diameter spheres. Other methods for making a particle are to dice, chop, or punch-out pieces of a hydrogel, e.g., dicing a sheet of hydrogel to make particles.

The hydrogels were also formed as filaments. Thin strands of hydrogel could be extruded from a nozzle, as demonstrated in Example 4 (see FIG. 3). The strands were formed independently or with an interior rod or fiber (see FIG. 4). A process for forming the strands may comprise adding dimethyl sulfoxide (DMSO) or other solvent of a similar nature that is substantially water soluble, for instance formamide, dimethyl formamide, 2-methyl-N-pyrollidinone (also known as NMP), and dioxane. The strands may be further processed. One example is a material made of a plurality of strands. The strands may be surrounded by another hydrogel or mixed with other materials. One embodiment is a matrix for cell culture or tissue engineering applications.

The hydrogels may be made to be substantially free of chemical crosslinks besides the disulfide bonds in the hydrogel. The term substantially free, in this context, means that there are no, or only a small percentage relative to the disulfide bonds, other crosslinking agents present in the hydrogel: for instance, no more than about 5% of other chemical crosslinks; artisans will immediately appreciate that all the ranges and values within the explicitly stated ranges are contemplated, e.g., no more than 0.1% or no more than 1%. The number of disulfide bonds in a hydrogel may be approximated for these purposes by estimating the total number of cysteine residues and assuming that they are all involved in a disulfide bond.

The hydrogels may be substantially free of exogenous crosslinking agents. Such agents are compounds with at least two functional groups that are each capable of binding to a keratin. Examples of exogenous crosslinking agents or their functional groups are glutaraldehydes, formaldehydes, succinimides, and maleimides. These are not needed to make hydrogels as described herein. The term substantially free, in this context, means that there are no, or only a small percentage of such crosslinkers relative to the disulfide bonds: for instance, no more than about 5%; artisans will immediately appreciate that all the ranges and values within the explicitly stated range are contemplated.

The hydrogels may be substantially free of derivatized sulfhydryl groups. For instance, they may be free of sulfonic acid and/or sulfonic acid and/or cysteic acids (meaning acids of a sulfhydryl on a cysteine amino acid). They may also be substantially free of permanently oxidized sulfhydryls, meaning that there are none, or not enough to prevent formation of a firm hydrogel with a modulus of more than about 5 Pa as described herein. The cysteine residues of the hydrogel may be substantially disposed as either participants in a disulfide bond or free sulfhydryls.

The hydrogels may be made so they are substantially only made of hair biomolecules. A patient's hair may be used, treated, and returned into the patient as a biomaterial without the addition of non-autologous hair biomolecules and/or without any non-autologous materials. Embodiments include hydrogels made with at least 90% hair biomolecules; artisans will immediately appreciate that all the ranges and values within the explicitly stated ranges are contemplated, e.g., at least about 95%, or at least about 98%. The percentages may be calculated as dry w/w meaning that the dry weight of the non-hair portion is represented as a percentage of the total dry weight of the hydrogel.

Incorporation of Therapeutic Agents and Bioactive Materials

A therapeutic agent may be included in a hydrogel. One method is to add the agent during manufacture. Another process is to load the agent into the hydrogel after its formation, for instance by swelling it in a first solvent containing the agent and de-swelling it in a second solvent. Examples of agents are antibiotics, antimycotics, anticancer agents, anti-inflammatory steroids and non-steroids, small molecule drugs, bioactive biomolecules, and growth factors, including growth factors that induce the formation of new bone, blood vessels, connective tissue, neural tissue, and those that accelerate healing such as factors derived from platelets.

Bioactive materials may be combined with the hydrogels during and/or after hydrogel formation. Further, it is beneficial in some applications to attach the agents and/or materials to an exterior of a hydrogel, either covalently or by adsorption. Useful spacers and attachment protocols are described for example by Greg T. Hermanson in a book entitled "Bioconjugate Techniques", 1996, Elsevier Science, Academic Press, hereby incorporated herein by reference. Many of these schemes involve reacting a nucleophilic functional group such as an amine or thiol with an electrophilic group, e.g., maleic acid or succinimide ester. Other functional groups for reaction are hydroxyls and carboxyls. Example 6 details an embodiment of a hydrogel modified with fibronectin that was successfully used for cell attachment and culture.

Some bioactive materials are useful for cell attachment or other uses. Examples include laminin, fibronectin, vitronectin, fibrin, MATRIGEL®, extracellular matrix molecules, or cell-specific-binding fragments of any of these. Further examples are cell adhesion peptides or cell binding fragments, e.g., comprising the tripeptide RGD. Further description of hydrogel modification for the purpose of interaction with cells is disclosed by Salinas C N and Anseth K S, "The influence of the RGD peptide motif and its contextual presentation in PEG gels on human mesenchymal stem cell viability", J Tissue Eng Regen Med. 2008 July; 2(5):296-304, hereby incorporated herein by reference.

Some binding techniques may be used that take advantage of the abundance of sulfhydryl and disulfide bonds available for reaction. Example 5 details such a process. The added biomolecules have one or more free sulfhydryls for reaction and are exposed to the hydrogels along with a reducing agent. Alternatively, a spacer with a thiol is introduced, with another group on the spacer being available for subsequent reaction. Embodiments for attachment include mixing a thiolated molecule (e.g., biomolecule, synthetic molecule, polymer, biopolymer) with a reducing agent and exposing a hydrogel to the reduced thiolated molecule and a reducing agent. The thiolated molecule may be bioactive and/or may be a spacer with a functional group for further reaction (e.g., amine, carboxyl, hydroxyl). Examples of spacers are polymers, hydrophilic polymers, e.g., polyethylene glycol and polyacrylic acid, and hydrophobic polymers, e.g., alkanes.

Incorporation of Living Materials

Cells may be integrated with the hydrogels. One approach involves preparing a hydrogel and exposing it to cells. The cells may attach and also grow on the hydrogels. The hydrogels may be planar or curved, e.g. a sheet or a microsphere. The hydrogels may be essentially pure hair biomolecules or may further include other materials, e.g., cell adhesion molecules. Example 6 (see FIG. 5) details an embodiment of a modified hydrogel successfully used for cell attachment and culture.

Examples of cells include fibroblasts, dermal papilla cells, keratinocytes, epithelial cells, progenitor cells and stem cells. When placed in a patient, the cells may be autologous to the patient, although other cells could be cultured as well. Applications involving pluripotent stem cells from particular tissues are detailed below, e.g., adipose pluripotent stem cells, epidermal pluripotent stem cells, and dermal pluripotent stem cells.

In some embodiments, a hydrogel as described herein is used to attach stem cells. The stem cells may be, for instance, adult stem cells. In another embodiment, the stem cells used are autologous adult stem cells. Useful cells for this purpose can be obtained from liposuction aspirate and/or from hair follicles. They can also be obtained from bone marrow, umbilical cord blood, menstrual blood, placenta, amniotic tissue, muscle, and other sources.

Shaped and Composite Hydrogels

The hydrogels may be prepared in a variety of shapes and sizes, for example: sheets, rods, particles, spheres, filaments, and discs. The hydrogels may also be formed on or all around other materials. Options for making materials include preparing a mold and pouring hair in a concentrated treatment solution into the mold, where the hydrogel will set and be formed into the mold shape. The hydrogel may further include other materials that are coated or encapsulated. For instance a hair or a polymer may be coated or surrounded with a hydrogel. Or a first material may be coated or encapsulated inside the hydrogel. For instance, a mesh or sheet may be coated with the hydrogel.

FIG. 6 depicts some embodiments of a hydrogel. FIG. 6A depicts hydrogel sheet 60. FIG. 6B depicts sheet 60 encapsulating mesh 62, which is completely enclosed. FIG. 6C depicts rod 64 of a material surrounded over a portion of its length by translucent hydrogel 66. FIG. 6D depicts a collection 68 of hydrogel microspheres 70. FIG. 6E depicts hydrogel filament 72. FIG. 6F depicts rod-shaped hydrogels 74 encapsulated within material 76, e.g., another hydrogel of the same or different material. FIG. 6G depicts hydrogel particles 78.

Applications for Hair Growth

Cosmetic surgical hair restoration is a proven technology that in the US generates over $800 million in revenue per year. This procedure simply harvests follicles from the back of the head and implants them in the front. Clearly this does not create new hair; it just redistributes the limited number of hair follicles located in the permanent fringe of hair (in males) that is resistant to pattern baldness. Hair multiplication has been proposed whereby only a few follicles are harvested, their stem cells extracted, the cells are cultured to grow more of them, and then the multiplied stem cells are converted into thousands of follicle-inducing implants. Speculation and authoritative pronouncements have been made since the late 1990s that cell-based hair restoration is imminently feasible, but, in fact, it has not been feasible.

Although the cells needed to achieve hair follicle neogenesis can be obtained by known means, there is currently a lack of enabling technology to create an effective cell construct. Enablement of the assembly of stein cells into hair follicle-inducing implants for the creation of new hair follicles (follicle neogenesis) is needed.

Figure 7:
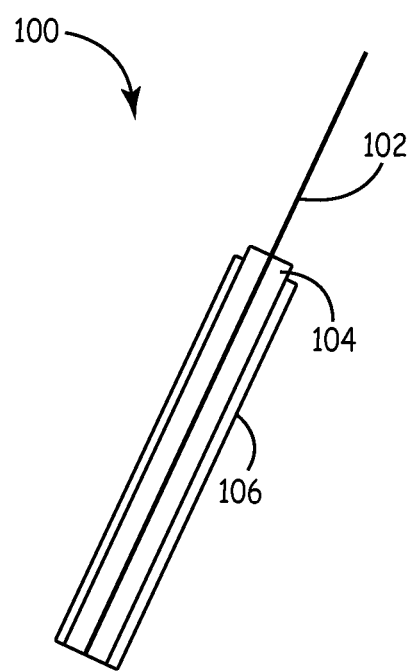
FIG. 7 depicts a hair construct for hair culture and implantation.

The methods and materials described herein address this problem and provide a coating for a percutaneous implant upon which dermal and epidermal stem cells can be seeded in concentric layers. FIG. 7 is a cross-sectional view of a hair follicle-inducting cell construct comprised of a hair (e.g., hair from the patient) coated with a hydrogel derived from (optionally autologous) hair and then invested first with a concentric layer of autologous hair follicle-derived epithelial stem cells and secondly with a concentric layer of dermal papilla (mesenchymal) stem cells. Construct 100 has hair 102 coated with first hydrogel 104 and second hydrogel 106. First, inner, hydrogel 104 comprises epidermal follicular stem cells. Second, outer, hydrogel 106 comprises dermal papilla cells.

Optionally all or essentially all of the ingredients are autologous, thereby providing improved clinical safety. Cut hair may provide a percutaneous implant core and the proteins for making the hydrogel. Autologous donated blood may be used to provide fibronectin for cell attachment-enhancement modification of the hydrogel and growth factor supplements that can be added to the cell culture media. And a scalp biopsy provides follicles for stein cell isolation and culture.

A strand of hair is a preferred starting material for making a cell construct implant because it simulates the proven technology of autologous whole follicle transplantation, in which the hair shaft protrudes from the implantation wound and is subsequently shed. Coating hair with an aqueous solution, however, presents a problem due to the natural water repellency of hair. Thus simply dipping hair into an aqueous solution results in beading instead of coating. This is an undesirable result because the coating is not consistently thin and distributed. As disclosed herein, however, a hydrogel may be uniformly coated over a hair or other rod. The hair follicle-inducing cells optimally are seeded in a uniformly concentric layer that is parallel to the shaft core in order to replicate the microarchitecture of a natural hair follicle.

Alternatively, a polymer or rod-shaped material may be used instead of hair 102. Or a single hydrogel comprising stem cells of various types may be used. Or one hydrogel could be used with stem cells on either side. Other cell attachment molecules or motifs may be used instead of the fibronectin.

Applications for a Dermal Filler

The market for dermal fillers is currently served by a wide variety of injectable substances, most notably those comprised of collagen or hyaluronic acid and its derivatives. None of these conventional injectable substances provide a lasting correction of tissue defects and wrinkles. More recently there has been a renewed interest in autologous fat transfer for cosmetic facial rejuvenation due to the popularity of liposuction for removal of unwanted fat and improvements in the technology of harvesting stein cells from liposuction aspirate. Fat transfer, however, suffers from great variability in achievement of the desired effects due to the unpredictability of its persistence. Moreover, obtaining suitable fat samples from the patient can be an unwanted extra step.

A recent study by Natesan S, et al. entitled "Adipose Derived Stem Cell Delivery into Collagen Gels using Chitosan Microspheres", *Tissue Eng Part A*. Nov. 16, 2009, incorporated herein by reference, has shown that liposuction-derived (adipose-derived) stem cells may be attached to microspheres for cell survival and engraftment. A hair biomolecule hydrogel as set forth herein can be provided as microspheres and serve as a delivery vehicle for attached stem cells, and/or other cells, to improve their survival and engraftment. For example, these may be used in fat transfer and dermal filler applications.

In use, a hydrogel as set forth herein, optionally in particulate form (e.g., spheres), is cultured with adipose-derived cells. The cells may comprise stem cells, or consist essentially of stem cells. The cultured cells are introduced into the patient as a dermal filler, typically by injection. Additionally, or alternatively, hydrogels with no cells may be used. The hydrogels may optionally include agents and/or attachment or growth factors.

Application in Wound Healing

A cell therapy dressing to accelerate the healing of chronic wounds, especially diabetic wounds, is a medically important and much needed area of therapy. Diabetic foot ulcers, which affect 15% of all people with diabetes at some point in their lives, are a leading cause of hospitalization among diabetic patients and often lead to amputation. These wounds are estimated to cost the U.S. health care system over $5 billion per year.

The healing rates for diabetic foot ulcers average from 12 to 20 weeks in clinical trials, but in practice these wounds often never heal. The longer the wound remains open the greater the risk of infection, wound enlargement, osteomyelitis, and ultimately the need for amputation. Diabetes currently affects over 20 million Americans or 7% of the population. Over 60% of the non-traumatic limb amputations in this country occurred among persons with diabetes. Other types of chronic wounds such as venous stasis ulcers and decubitus (bed sore) ulcers can also be addressed by the method described herein.

A somewhat related problem is severe burns. In this case the patient previously may have been in good health, but the severity of the trauma overwhelms the body's capacity for normal healing and the price of survival is disfiguring scars. Wound contraction and scar formation in fact are the opposite extreme of abnormal healing in comparison to chronic wounds. Yet both problems involve excessive inflammation and a lack of regenerative healing. The stem cell therapy products using the hydrogel described herein address these problems by providing mitigation of excessive inflammation and preparation of the injured tissue for an orderly regenerative healing process with reduced scar formation.

Accordingly, an embodiment of the present invention is a wound contacting dressing to be applied on wounds (e.g. after wound debridement and control of infection, if required). The wounds may be chronic, diabetic, ulcerous, from venous stasis, or burns, for instance. The dressing may comprise a hydrogel as set forth herein. The hydrogel may comprise a cell and/or agent and/or factor as already disclosed.

One embodiment is to culture cells on the hydrogel and apply the hydrogel to the wound. The hydrogel may be microspheres and the cells stem cells; in use, the cultured cells are placed in the wound site. A covering may be applied thereupon. Further, a covering may be placed over the particles and in intimate contact with the wound. The covering may be permeable to air and/or fluids and not permeable to the cells and/or the particles. For instance, a sheet of a hair biomolecule hydrogel may be applied to the wound after particles of cell-bearing hydrogel have been applied. The sheet may comprise a mesh. The mesh may be sized to contain the stem cells or be more open and allow cells to pass but contain microparticles. The mesh may be coated with a hydrogel that either encapsulates it completely or partially. The mesh may furthermore have openings in between its coated fibers, with the hydrogel being an adherent thin layer than does not bridge-over the mesh gaps.

Figure 8:
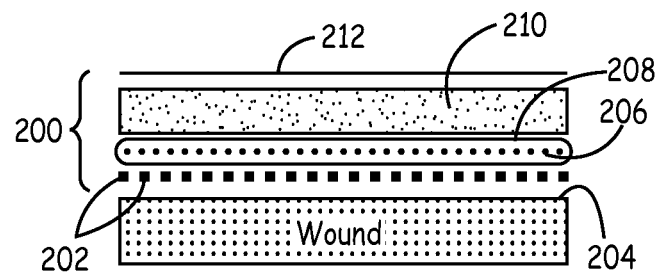
FIG. 8 depicts a wound treatment system.

An embodiment of a dressing system 200 is illustrated in FIG. 8. Applied stem cells 202 are in direct, intimate contact with wound surface 204. Cells 202 are optionally attached to denatured hair biomolecule hydrogel 208, which may comprise porous mesh 206. The next layer of the dressing is an optional absorbent material 210 designed to absorb fluid that exudes from wound 204 and through the porous layers beneath. Material 210 may be changed daily as required without disturbing the underlying layers, which can remain in contact with the wound to stimulate regenerative healing. The top layer 210 is an optional covering. In use, cells recovered from the patient are cultured on hydrogel 208, which is then applied to wound surface 204. Absorbent material 210 is overlain and secured. Hydrogel 208 may be treated with autologous materials, for example: one or more of autologous serum, albumin, fibronectin, fibrin, fibrinogen, vitronectin, blood plasma, and platelets.

Figure 9:
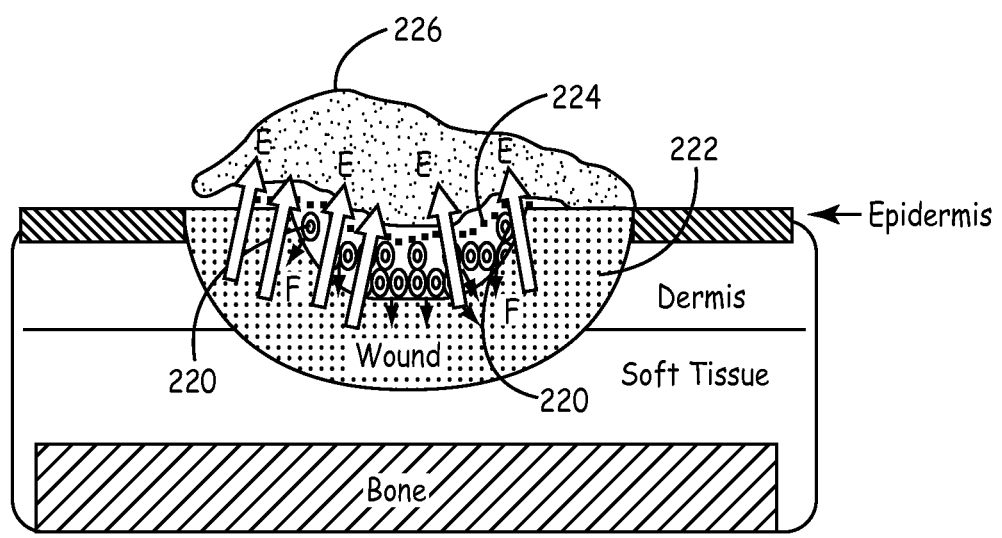
FIG. 9 depicts an alternative wound treatment system.

Another embodiment is a dressing in which stem cells are attached to a hydrogel in the form of microspheres. As illustrated in FIG. 9, stem cell-seeded microspheres 220 first are administered to provide coverage and intimate contact with wound 222. The living stem cells release factors that stimulate wound healing (arrows F pointing into the wound) while allowing wound exudate (arrows E pointing out of wound) to flow out of the wound, through an applied microsphere-retentive hydrogel 224 (dashed lines) and into overlying absorbent dressing material 226. Hydrogel 224 optionally comprises a mesh, e.g., nylon.

EXAMPLES

Example 1

Formation of Hydrogel

A batch of Shindai protein extract, which is a hair protein extract solution (HPE), was concentrated in an ultra-filtration cell, using a 10,000 molecular weight cut-off ultra-filtration membrane in an AMICON® stirred cell at 30 psi overnight. Approximately 50 ml of HPE were concentrated to about 5 ml of a viscous hair protein extract concentrate, hereinafter "$HPE_c$", which had the consistency and color of pancake syrup. The $HPE_c$ was then converted to hydrogel following the steps below:

1. Providing filtered HPE via the Shindai method,
2. Concentrating the HPE by ultra-filtration to obtain $HPE_c$,
3. Coating the $HPE_c$ onto a surface or substrate, 4. Allowing the $HPE_c$ to dry in open air just to the stage of dryness such that further drying would cause dissolved urea to crystallize, 5. Hydrating the resultant air dried film by exposing it to high humidity or aqueous media, optionally containing an oxidizing agent, for example hydrogen peroxide, 6. Exhaustively extracting the resultant hydrogel with water to remove all residual urea, thiourea, and mercaptoethanol.

Figure 6A:
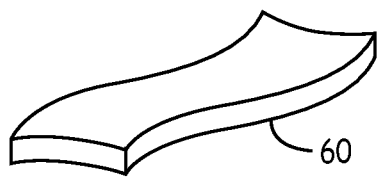
FIGS. 6A to 6G depict various shapes for a hydrogel.
Figure 6B:
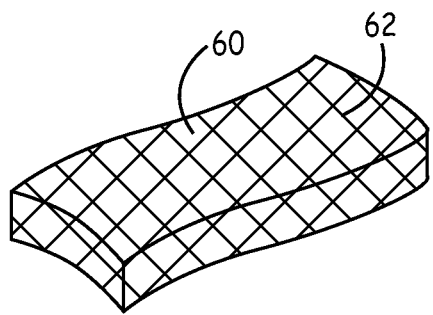
Figure 6C:
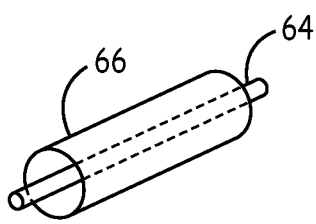
Figure 6D:
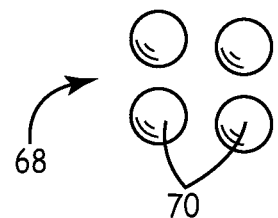
Figure 6E:
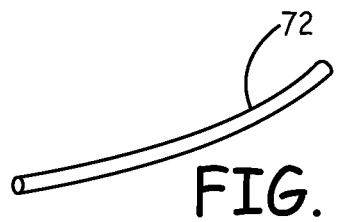
Figure 6F:
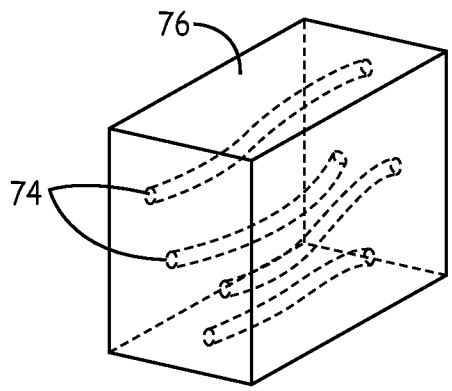
Figure 6G:
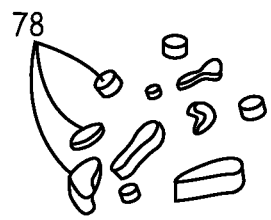

The hydrogel obtained by this process, after being dried to a solid in air, rehydrates upon soaking in deionized water to produce a gel that contains about 50 to about 60% water. A fully hydrated $HPE_c$-hydrogel is crystal clear with good physical integrity and can be cut into shapes as shown in FIG. 1 or 6G.

Example 2

Failure to Form a Hydrogel

Alternative approaches did not result in formation of a hydrogel. A material was made by the same process as set forth in Example 1 except that oxidized hair was used instead of HPE from Shindai method. Specifically, a peracetic acid treatment of hair as described in U.S. Pat. No. 6,159,496 caused substantial bleaching of the hair and weakening of the fibers. Subsequent extraction and concentration via ultrafiltration as per the steps of Example 1 gave a lower yield of a lower viscosity concentrate, and a weak, friable jelly. This material was not a hydrogel with sufficient physical integrity and strength to allow processing into test materials comparable to an $HPE_c$-hydrogel. The oxidative treatment of U.S. Pat. No. 6,159,496 likely caused substantial damage to the proteins beyond the simple oxidation of cysteine to cysteic acid.

Example 3

Hydrogel Microparticles

An $HPE_c$ hydrogel (see Example 1) can be produced in the form of microspheres that can provide a delivery vehicle for attached stem cells to improve their survival and engraftment in fat transfer and dermal filler applications. Specifically, 1.5 ml of $HPE_c$ was poured into 250 ml of peanut oil with mixing at a moderate speed by means of an overhead motor-driven stainless steel impeller. After about 2 hours the stirring was stopped and the oil kept undisturbed. After settling for about 4 hours, the bulk of the oil was decanted and the remaining portion examined under the dissecting microscope and discovered to contain perfectly formed spheres of $HPE_c$ hydrogel. While not wishing to be bound by any specific theory, it can be rationalized that the liquid droplets converted into gel because of transfer of mercaptoethanol from the droplets into the oil or by transfer of oxygen from the oil into the droplets. Thus any alterations to the composition of the oil phase based upon such theory that would accelerate this discovered conversion of $HPE_c$ into hydrogel microspheres, such as addition of an oxidizing agent, are within the scope of this embodiment.

Figure 2A:
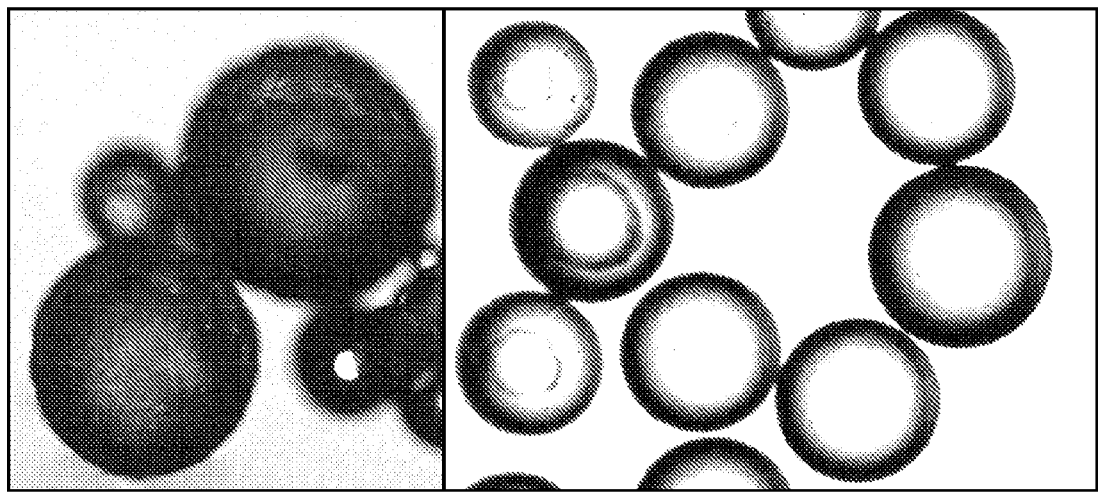
FIG. 2A is a photomicrograph montage showing a side-by-side comparison of denatured hair biomolecule hydrogel microspheres (left side) and collagen-coated polystyrene beads (right side) (10× original magnification); hydrogel microspheres are about double the size of the 125-212 µm commercial beads.

For example, the above procedure was repeated with the addition of 10 mL of a 10% (w/v) solution of benzoyl peroxide in toluene to the oil. The resultant microspheres were more easily collected on filter paper upon filtration of the oil. These microspheres were rinsed with hexane to remove oil, dried, and then resuspended in distilled water. A sample of the $HPE_c$-hydrogel microspheres obtained by this procedure in comparison to commercially available cell culture microspheres is shown in FIG. 2A.

Example 4

Hydrogel Filaments

Another unexpected discovery was made that allows $HPE_c$ to be thickened into an extrudable semi-solid. Addition of dimethyl sulfoxide (DMSO) to $HPE_c$ initially resulted in a decrease in viscosity, as expected. Surprisingly, there was soon a reversal of thinning and the mix rapidly thickened.

Figure 4:
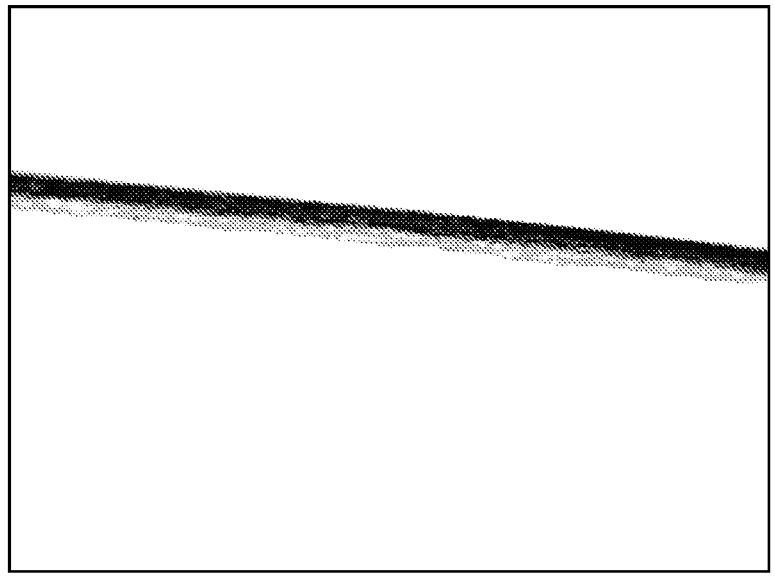
FIG. 4 depicts a hair with a uniform and smooth hydrogel coating.

These results allowed for a process of casting around an object. By placing a hair inside a 27 gauge hypodermic needle and expressing DMSO-thickened $HPE_c$ via an attached syringe it was possible to eject the hair from the needle such that the hair was uniformly covered with gel and bead-free, as shown in FIG. 4. Subjecting such coated hair to the above mentioned processing Steps 4, 5, and 6, will cause the water soluble DMSO to be leached out along with the other $HPE_c$ ingredients needing to be removed, thereby providing the desired scaffold for tissue engineered hair. This scaffold can then be processed further as desired for surface modification with appropriate biomolecules.

Figure 3:
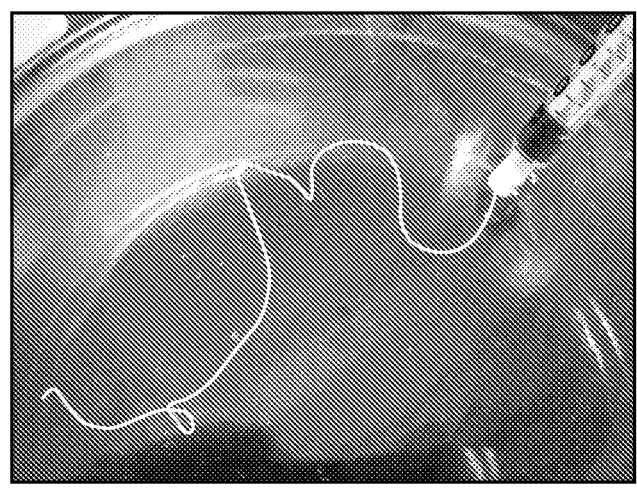
FIG. 3 depicts a filament of hydrogel being extruded through a nozzle of a syringe.

The unexpected and surprising effect of DMSO on $HPE_c$ was further illustrated by simply "dry spinning" a filament off the end of a syringe containing this new material. The airdried filament was soaked in dilute peroxide, as shown in FIG. 3, and exhibited unexpected physical integrity.

Example 5

Incorporation of Biomolecules

Biomolecules that contain sulfhydryl functionality can be incorporated into a hydrogel network of biomolecules comprising sulfhydryl groups and/or disulfide bonds as disclosed herein. For instance, the following steps may be used.

A. Providing an $HPE_c$-hydrogel using the process disclosed in Example 1,

B. Providing a solution of biomolecules wherein the biomolecule contains inter- and/or intra-molecular disulfide linkages and/or free sulfhydryl groups, e.g. natural or synthetic proteins, C. Adding mercaptoethanol or other reducing agent of similar reducing capability to the solution of step B, D. Combining the solution of step C with the hydrogel of step A and allowing the combined materials to soak for a period of time, E. Removing the treated hydrogel of step D from the solution of step C, rinsing with water or diluted hydrogen peroxide, and storing in 70% isopropanol or other suitable disinfectant until needed for further processing.

Example 6

Cell Attachment to Surface Modified Hydrogel

A hydrogel modification process may include chemically grafting a spacer molecule onto the hydrogel followed by covalent coupling of cell attachment-enhancing biomolecules such as RGD motifs onto the pendant spacer end groups. For example after Step 4 and before Step 5 of Example 1, a solution of mercaptoundecanoic acid (MUA) containing mercaptoethanol at high pH can be added to the $HPE_c$-hydrogel. The mercapto end of the MUA becomes bound into the mixed disulfide crosslinked structure of the gel and the carboxylic acid end is free for additional chemical modification to activate it towards engraftment of cell attachment-enhancing biomolecules.

Figure 5:
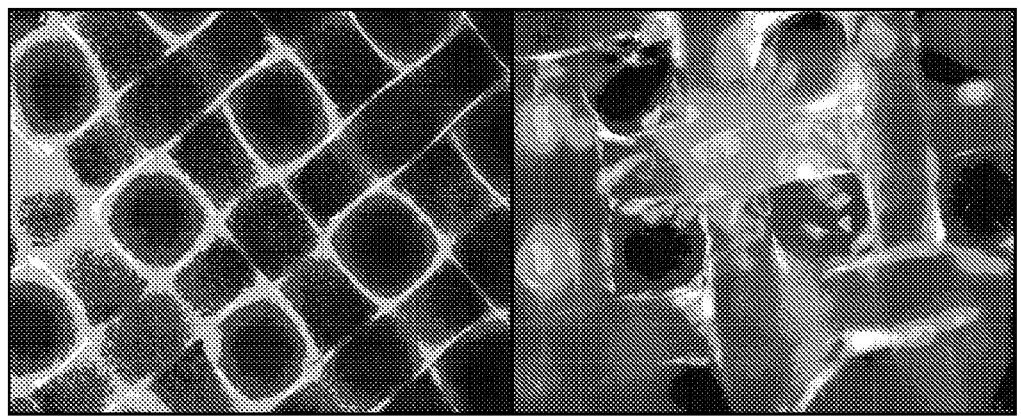
FIG. 5 is a photomicrograph montage showing an untreated nylon mesh wound contact layer (left side) that was non adhesive to cells, but provided for ready cellular attachment after the mesh was coated with a denatured hair biomolecule hydrogel featuring surface modification with fibronectin (right side)

Specifically, the $HPE_c$ solution was coated onto a glass slide and covered with a piece of nylon mesh (3M TEGADERM® wound contact layer). Additional $HPE_c$ was placed on top of the nylon and brushed to give a uniform coating. The $HPE_c$ was allowed to dry just until the liquid became tacky. Then a solution of MUA (5 mg/ml) in 1N ammonium hydroxide containing 5% mercaptoethanol was flooded over the surface of the $HPE_c$ residue and allowed partially to dry to form a composite. The composite was then soaked in 3% aqueous hydrogen peroxide solution for one hour to convert the dried $HPE_c$ solution into $HPE_c$-hydrogel. A control sample was prepared concomitantly in the same manner except without treatment with MUA. The samples were removed from the glass and suspended in 3 liters of deionized water with stirring overnight to extract all traces of mercaptoethanol, urea, and thiourea. Discs (6 mm diameter) were cut from each sample, allowed to dry, and then incubated in a 9:1 (v/v) mixture of acetone:water containing 5 mg/ml of a water soluble carbodiimide (N,N'-ethyldiisopropyl carbodiimide) for one hour. The samples were rinsed with sterile phosphate buffer (PBS) and incubated with 1 mg/ml bovine serum fibronectin for 20 min. The samples were again rinsed with PBS, placed in polyhydroxyethyl methacrylate (hereinafter "polyHEMA") coated 24-well culture plates. The samples were fixed to the bottom of the wells by first adding methanol to the wells to tackify the polyHEMA, then allowing the methanol to evaporate in the biological safety cabinet. The samples were then covered with culture media comprised of DMEM (Dulbecco's minimum essential culture medium) containing 10% FBS (fetal bovine serum) and seeded with human foreskin fibroblasts that had been pre-incubated with CELL-TRACKER® red fluorescent dye. As shown in FIG. 5, samples of this hydrogel provided a good substrate for cell attachment. Control samples of untreated nylon, $HPE_c$-hydrogel coated nylon without any further treatment, and $HPE_c$-hydrogel coated nylon incubated with fibronectin but without pretreatment with MUA did not exhibit significant evidence of cell attachment.

Example 7

Cell Attachment to $HPE_c$-Hydrogel Microspheres

Figure 2B:
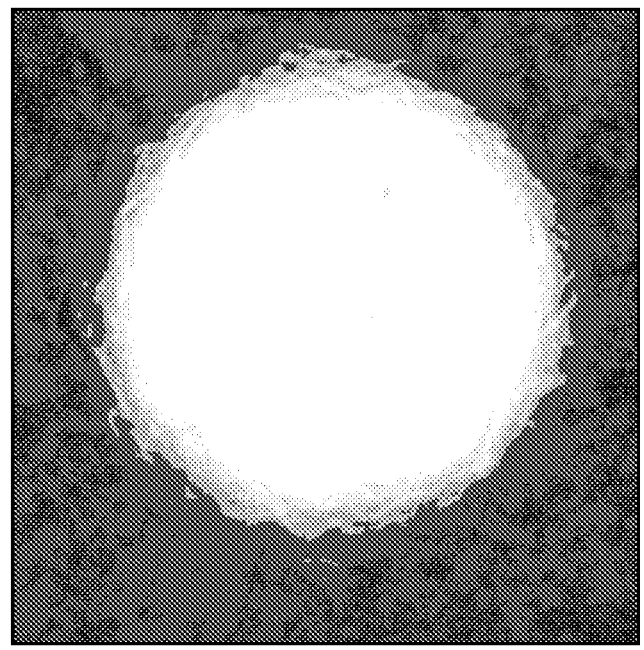
FIG. 2B is a photomicrograph of a denatured hair biomolecule hydrogel microsphere in which fluorescently labeled human fibroblasts are attached to the surface (auto-fluorescence of the hydrogel itself interferes with viewing of the cells, which in this image can be seen completely surrounding the surface of the microspheres)

Microspheres prepared as described in Example 3 were incubated with red fluorescent dye as described in Example 6 except that the 24-well plate wells were not coated with polyHEMA. Instead, the cells and microspheres both were allowed to settle undisturbed to the bottom of the well and left undisturbed in the 5% carbon dioxide, 37° C. cell culture incubator for 3 days. The microspheres were gently retrieved with a pipette and placed in a fresh well with fresh media for 3 more days. Upon inspection, as shown in FIG. 2B, cells completely surrounded the microspheres. It was discovered, however, that cell attachment was only detectable using samples of microspheres that had been previously extracted for at least one overnight period in a large volume of water. A thorough extraction of the microspheres was thus effective to remove all traces of urea and other components of the hair treatment solution.

All publications and patent applications set forth herein are hereby incorporated herein by reference for all purposes; in case of conflict, the specification is controlling. Headers herein are provided in the text for convenience of the reader but do not limit the scope of the disclosure. Various embodiments are described with particular features. In general, these features may be mixed and matched to make further embodiments.

The invention claimed is:

1. A clear hydrogel substantially free of cysteic acid moieties comprising a network of denatured human hair biomolecules being intermolecularly crosslinked with disulfide bonds to form the hydrogel with a modulus of more than about 100 Pa, wherein the hydrogel is substantially free of chemical crosslinks other than the disulfide bonds between the human hair biomolecules.

2. The hydrogel of claim 1 with the cysteine residues of the hydrogel being substantially disposed as either participants in a disulfide bond or free sulfhydryls.

3. The hydrogel of claim 1 being substantially free of sulfonic acid and sulfinic acid.

4. The hydrogel of claim 1 wherein the hair biomolecules provide at least about 90% of the network of the hydrogel, as measurable by dry w/w.

5. The hydrogel of claim 1 wherein the hydrogel comprises at least about 98% hair biomolecules as measurable by dry w/w.

6. The hydrogel of claim 1 wherein the network of denatured human hair biomolecules is essentially free of non-hair ingredients.

7. The hydrogel of claim 1 wherein the hydrogel further comprises a therapeutic agent.

8. The hydrogel of claim 7 wherein the therapeutic agent is covalently attached to the network of denatured human hair biomolecules.

9. The hydrogel of claim 1 wherein the hydrogel comprises at least about 40% w/w water.

10. A material comprising a plurality of particles formed from the hydrogel of claim 1.

11. A biomedical system for treating a wound comprising a clear hydrogel that comprises a network of denatured human hair biomolecules intermolecularly crosslinked with disulfide bonds to form the hydrogel with a modulus of more than about 100 Pa wherein the hydrogel is substantially free of cysteic acid moieties.

12. The system of claim 11, wherein the hydrogel is substantially free of chemical crosslinks other than the disulfide bonds between the human hair biomolecules.

13. The system of claim 11 further comprising cells attached to the hydrogel.

14. The system of claim 13 wherein the cells are stem cells.

15. The system of claim 11 wherein the hydrogel comprises a plurality of hydrogel particles.

16. The system of claim 15 wherein the particles are microspheres.

17. The system of claim 11 further comprising a covering permeable to oxygen and fluid, with the covering being non-permeable to vertebrate cells.

18. The system of claim 11 further comprising a sheet associated with the hydrogel.

19. The system of claim 18 wherein the sheet comprises a plastic mesh.

20. The system of claim 14, wherein the stem cells are adipose-derived stem cells.

21. The system of claim 14, wherein the stem cells are hair follicle-derived stem cells.

22. The system of claim 14, wherein the stem cells are allogeneic and/or autologous.

23. The system of claim 11, wherein the hydrogel comprises a plurality of hydrogel particles that are seeded with stem cells.

24. The system of claim 23, wherein the stem cells are human adipose-derived stem cells.

25. The system of claim 24, wherein the stem cells are allogeneic and/or autologous.

26. The system of claim 23 further comprising a covering permeable to oxygen and fluid, with the covering being non-permeable to vertebrate cells and capable of retaining the hydrogel particles.

27. The system of claim 23, wherein the plurality of hydrogel particles seeded with stem cells are dispersed in a filler.

28. The system of claim 27, wherein the filler is a hydrogel.

29. The system of claim 28, wherein the hydrogel is hyaluronic acid.

* * * * *